US006852124B2

United States Patent
Cox et al.

(10) Patent No.: US 6,852,124 B2
(45) Date of Patent: Feb. 8, 2005

(54) VARIABLE STRENGTH STENT

(75) Inventors: Daniel L. Cox, Palo Alto, CA (US); Timothy A. Limon, Cupertino, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 10/244,198

(22) Filed: Sep. 16, 2002

(65) Prior Publication Data

US 2003/0023301 A1 Jan. 30, 2003

Related U.S. Application Data

(60) Continuation of application No. 09/877,305, filed on Jun. 7, 2001, now Pat. No. 6,468,302, which is a division of application No. 09/298,063, filed on Apr. 22, 1999, now Pat. No. 6,273,911.

(51) Int. Cl.[7] .................................................. A61F 2/06
(52) U.S. Cl. ........................................ 623/1.15; 623/1.3
(58) Field of Search .............................. 623/1.13–1.2, 623/101, 1.15, 1.16–1.22

(56) References Cited

U.S. PATENT DOCUMENTS

| 4,241,146 A | 12/1980 | Sivachenko et al. |
| 4,665,906 A | 5/1987 | Jervis |
| 4,725,334 A | 2/1988 | Brimm |
| 4,986,831 A | 1/1991 | King et al. |
| 5,019,090 A | 5/1991 | Pinchuk |
| 5,064,435 A | 11/1991 | Porter |
| 5,067,957 A | 11/1991 | Jervis |
| 5,108,417 A | 4/1992 | Sawyer |
| 5,133,732 A | * 7/1992 | Wiktor ....................... 623/1.22 |
| 5,135,536 A | * 8/1992 | Hillstead ..................... 606/195 |
| 5,195,984 A | 3/1993 | Schatz |
| 5,344,425 A | 9/1994 | Sawyer |
| 5,354,308 A | 10/1994 | Simon et al. |
| 5,383,892 A | 1/1995 | Cardon et al. |
| 5,395,390 A | 3/1995 | Simon et al. |
| 5,413,597 A | 5/1995 | Krajicek |

(List continued on next page.)

FOREIGN PATENT DOCUMENTS

| DE | 19537872 | 4/1997 |
| EP | 0 201 466 A2 | 4/1986 |

(List continued on next page.)

OTHER PUBLICATIONS

U.S. Appl. No. 08/630,787, filed Apr. 10, 1996.
U.S. Appl. No. 08/943,992, filed Oct. 3, 1997.

*Primary Examiner*—Corrine McDermott
(74) *Attorney, Agent, or Firm*—Fulwider Patton Lee & Utecht, LLP

(57) ABSTRACT

An expandable stent for implantation in a body lumen, such as an artery, is disclosed. The stent consists of a plurality of radially expandable cylindrical elements generally aligned on a common longitudinal stent axis and interconnected by one or more interconnecting members placed so that the stent is flexible in the longitudinal direction. The strength of the stent at a center section or at either end can be varied by increasing the mass of the struts forming each cylindrical element in that center section or end section relative to the lower mass struts in the remaining sections of the stent. Increasing the mass of the struts can be accomplished by, for a given strut thickness, increasing the width of the strut, or increasing the length of a cylindrical element.

6 Claims, 6 Drawing Sheets

U.S. PATENT DOCUMENTS

| | | |
|---|---|---|
| 5,449,373 A | 9/1995 | Pinchasik et al. |
| 5,475,506 A | 12/1995 | Kwon et al. |
| 5,514,154 A | 5/1996 | Lau et al. |
| 5,527,324 A | 6/1996 | Krantz et al. |
| 5,540,712 A | 7/1996 | Kleshinski et al. |
| 5,569,295 A | 10/1996 | Lam |
| 5,693,089 A | 12/1997 | Inoue |
| 5,716,393 A | 2/1998 | Lindenberg et al. |
| 5,741,327 A | 4/1998 | Frantzen |
| 5,746,765 A | 5/1998 | Kleshinski et al. |
| 5,776,161 A | 7/1998 | Globerman |
| 5,800,526 A | 9/1998 | Anderson et al. |
| 5,810,868 A | 9/1998 | Lashinski et al. |
| 5,827,321 A | 10/1998 | Roubin et al. |
| 5,836,966 A | 11/1998 | St. Germain |
| 5,855,600 A | 1/1999 | Alt |
| 5,861,027 A | 1/1999 | Trapp |
| 5,906,640 A | 5/1999 | Penn et al. |
| 5,911,754 A | 6/1999 | Kanesaka et al. |
| 5,922,021 A | 7/1999 | Jang |
| 5,925,061 A | 7/1999 | Ogi et al. |
| 5,938,697 A | 8/1999 | Killion et al. |
| 5,948,016 A | 9/1999 | Jang |
| 5,954,743 A | 9/1999 | Jang |
| 5,980,552 A | 11/1999 | Pinchasik et al. |
| 6,010,539 A | 1/2000 | Del Pesco |
| 6,017,365 A | 1/2000 | Von Oepen |
| 6,033,435 A | 3/2000 | Penn et al. |
| 6,042,597 A | 3/2000 | Kveen et al. |
| 6,042,606 A | 3/2000 | Frantzen |
| 6,048,361 A | 4/2000 | Von Oepen |
| 6,059,822 A * | 5/2000 | Kanesaka et al. .......... 623/1.15 |
| 6,066,168 A | 5/2000 | Lau et al. |
| 6,071,298 A | 6/2000 | Lashinski et al. |
| 6,071,308 A | 6/2000 | Ballou et al. |
| 6,106,548 A | 8/2000 | Roubin et al. |
| 6,146,403 A | 11/2000 | St. Germain |
| 6,159,238 A | 12/2000 | Killion et al. |
| 6,179,867 B1 | 1/2001 | Cox |
| 6,183,506 B1 | 2/2001 | Penn et al. |
| 6,200,337 B1 | 3/2001 | Moriuchi et al. |
| 6,206,910 B1 | 3/2001 | Berry et al. |
| 6,217,608 B1 | 4/2001 | Penn et al. |
| 6,231,598 B1 | 5/2001 | Berry et al. |
| 6,273,901 B1 | 8/2001 | Whitcher et al. |
| 6,273,910 B1 * | 8/2001 | Limon ....................... 623/1.15 |
| 6,273,911 B1 | 8/2001 | Cox et al. |
| 6,287,336 B1 | 9/2001 | Globerman et al. |
| 6,340,366 B2 | 1/2002 | Wijay |
| 6,344,055 B1 | 2/2002 | Shukov |
| 6,468,302 B2 * | 10/2002 | Cox et al. .................. 623/1.15 |
| 2001/0029397 A1 | 10/2001 | Thompson |
| 2001/0041929 A1 | 11/2001 | Von Oepen |
| 2002/0007212 A1 | 1/2002 | Brown et al. |

FOREIGN PATENT DOCUMENTS

| | | |
|---|---|---|
| EP | 0 540 290 A2 | 5/1993 |
| EP | 0 541 443 A2 | 5/1993 |
| EP | 0 606 165 A1 | 7/1994 |
| EP | 0 688 545 A1 | 12/1995 |
| EP | 0 800 801 A1 | 10/1997 |
| WO | WO 94/17754 | 8/1994 |
| WO | WO 95/23563 | 9/1995 |
| WO | WO 95/26695 | 10/1995 |
| WO | WO 96/09013 | 3/1996 |
| WO | WO 96/26689 | 9/1996 |
| WO | WO 98/22159 | 5/1998 |
| WO | WO 98/48734 | 11/1998 |
| WO | WO 99/02105 | 1/1999 |

\* cited by examiner

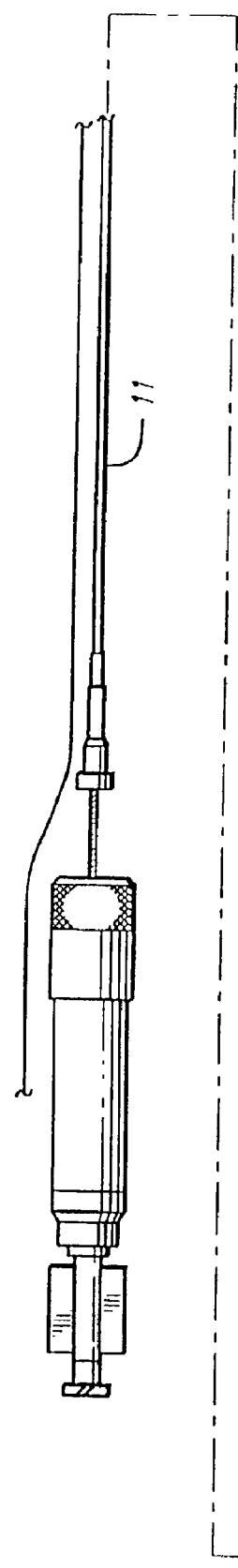
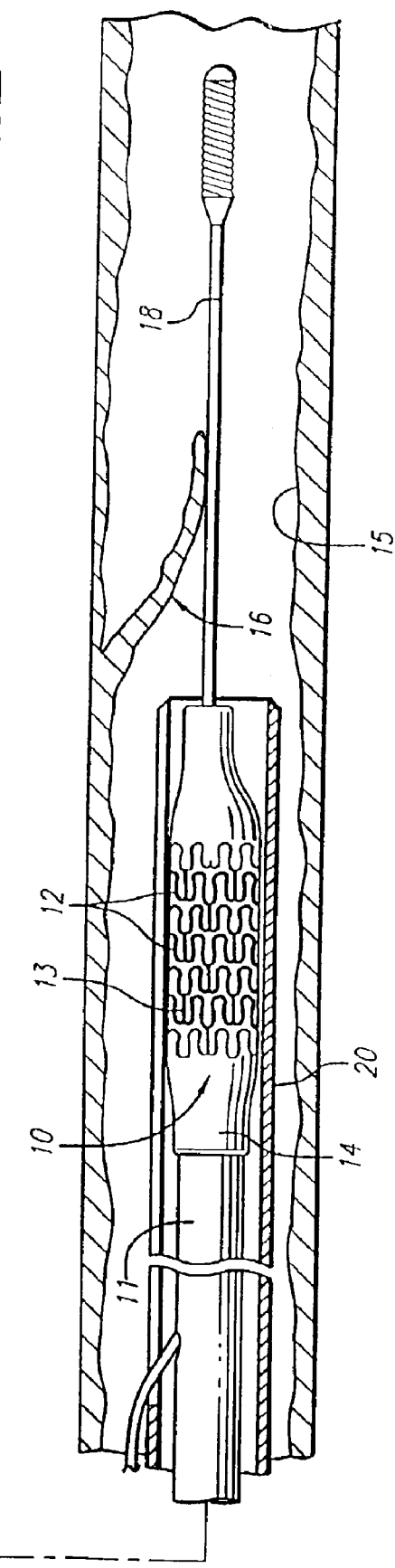
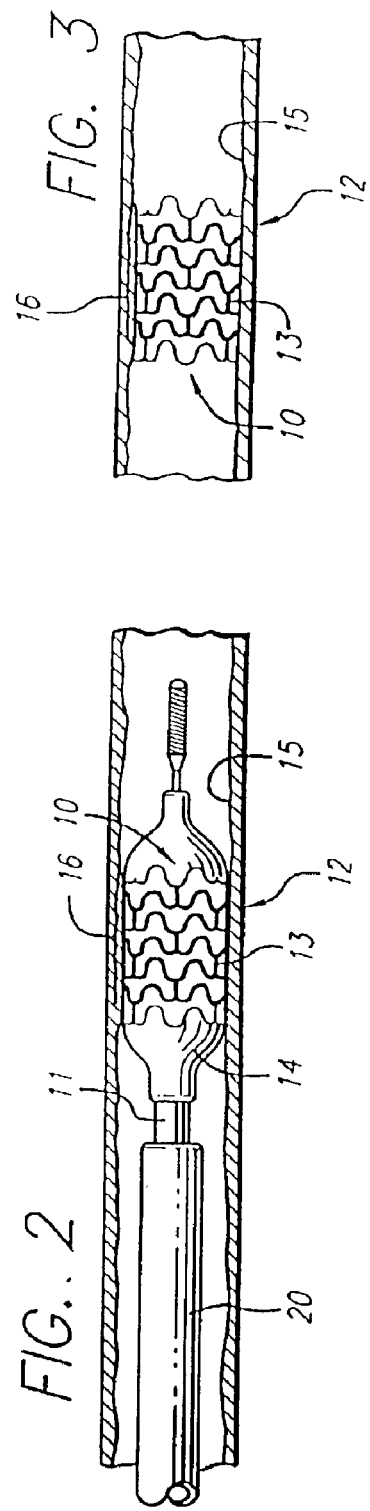

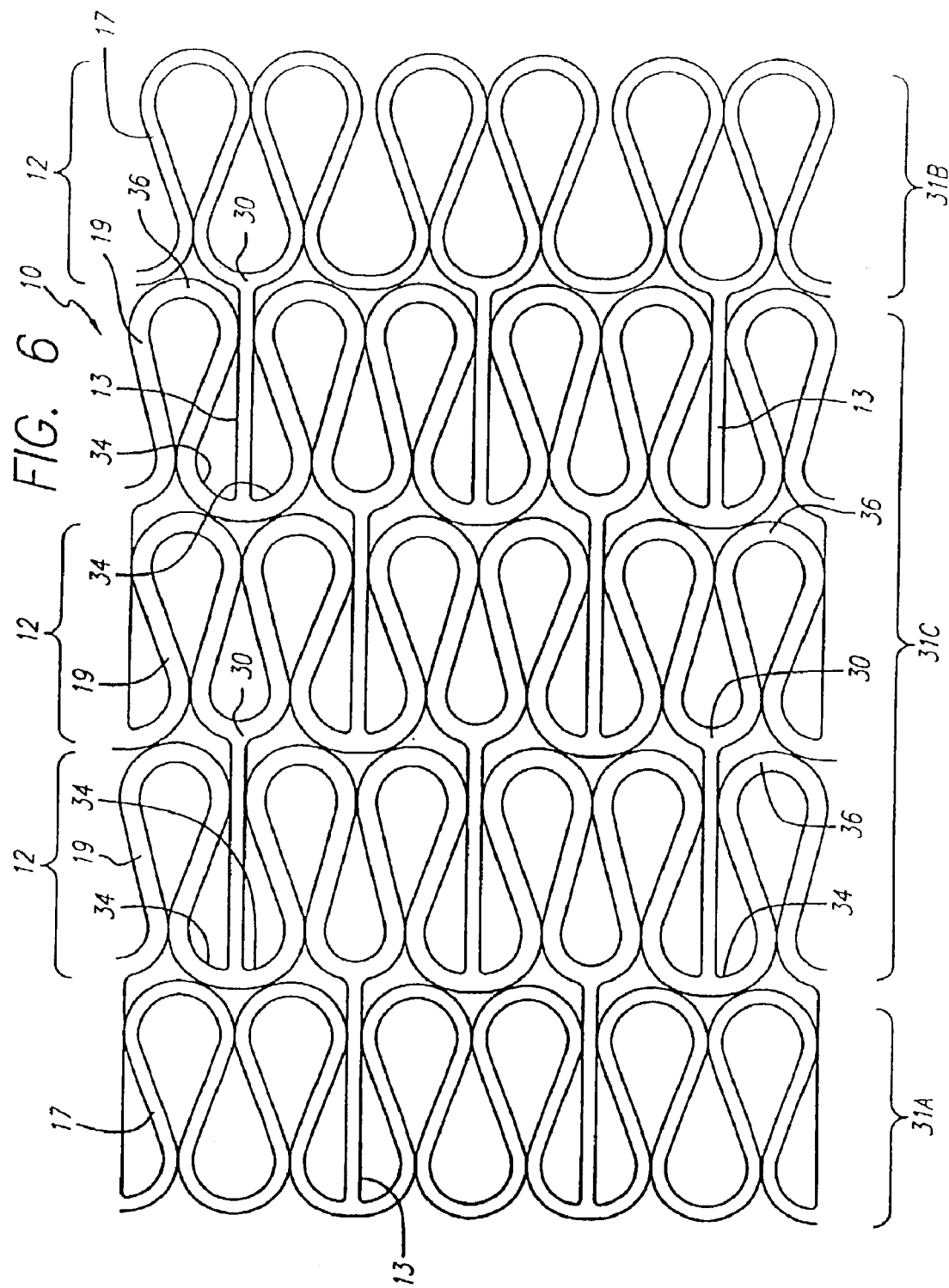

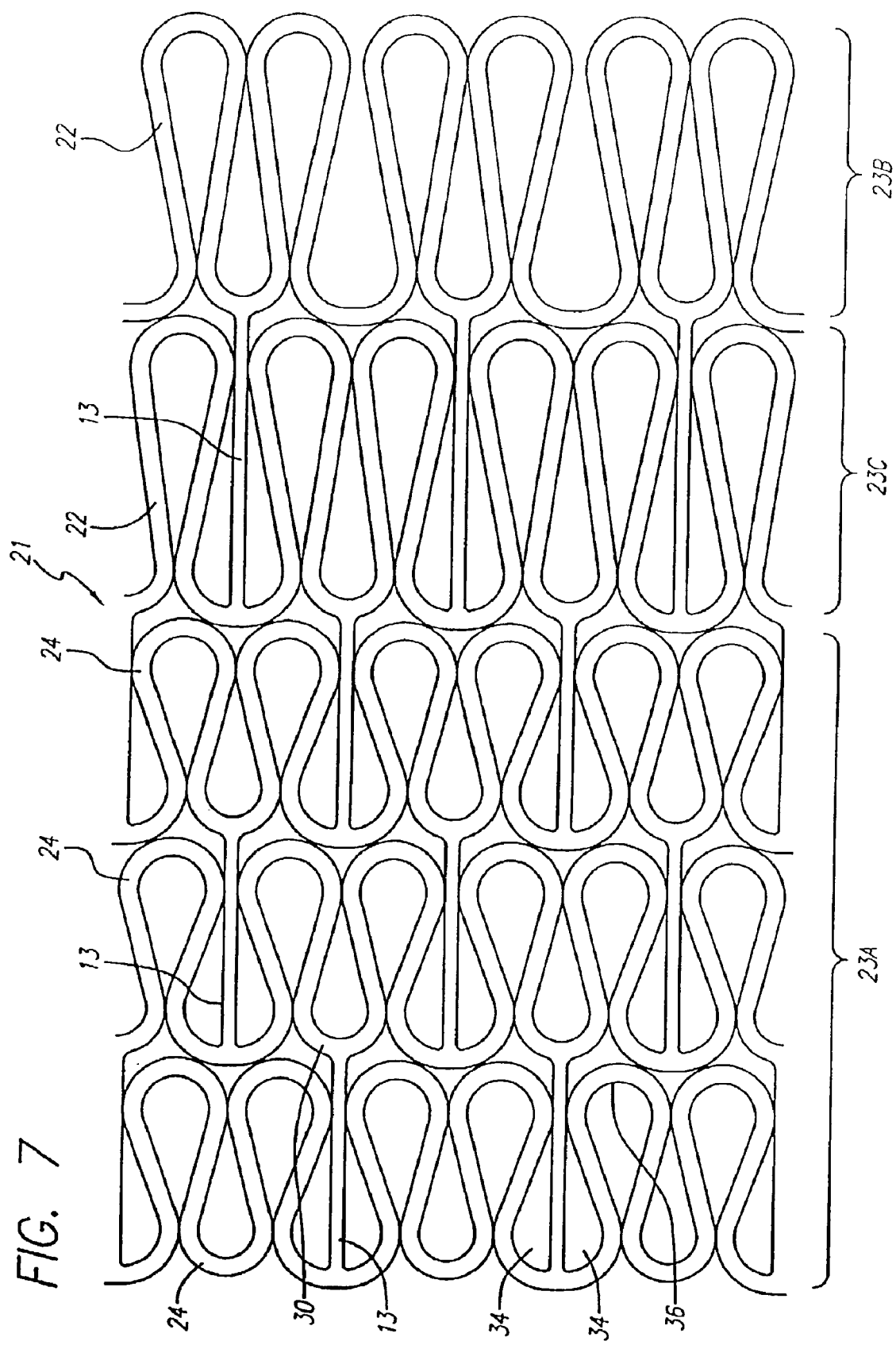

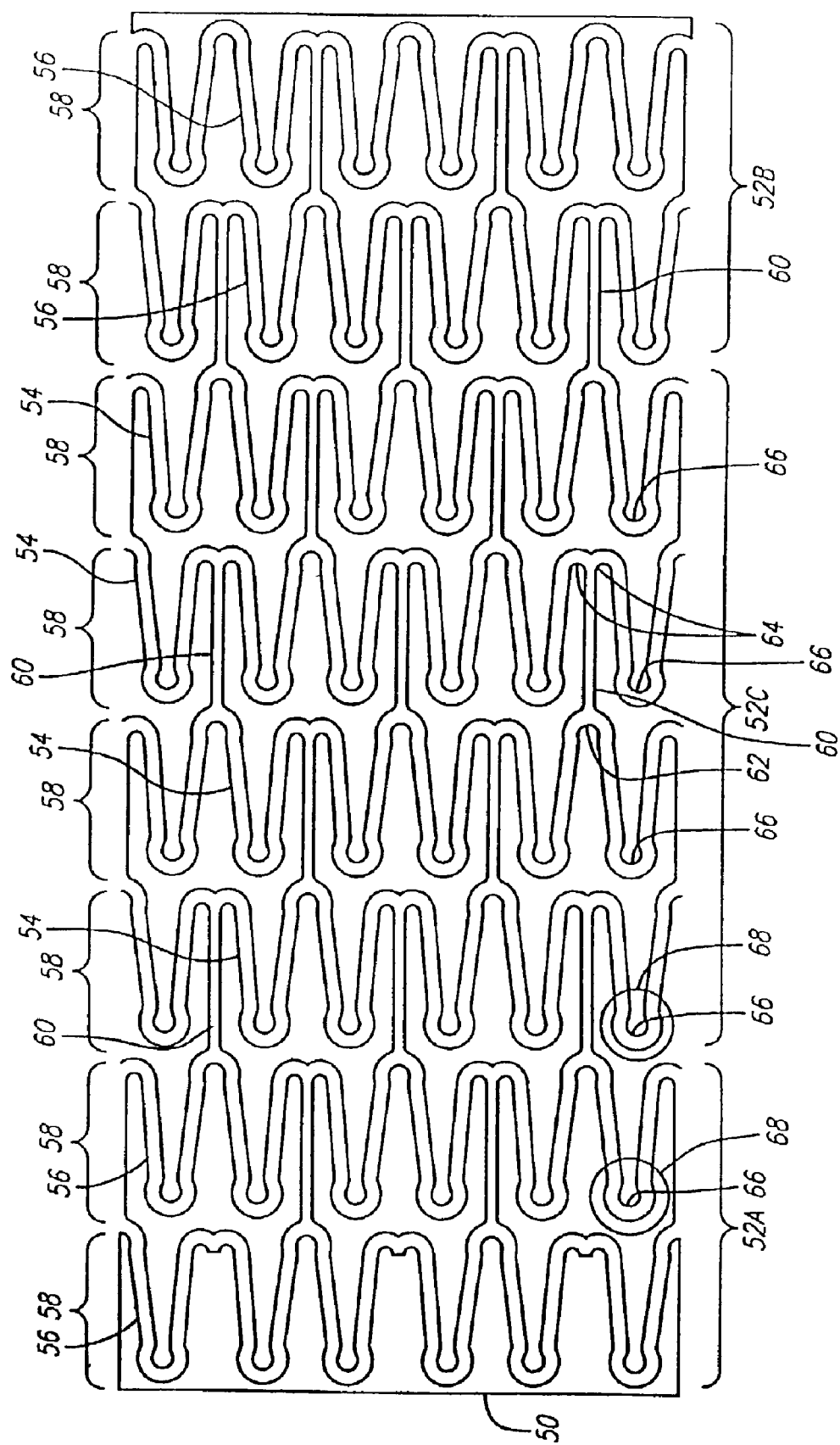

VARIABLE STRENGTH STENT

This is a continuation application of parent application having U.S. Ser. No. 09/877,305, filed Jun. 7, 2001, now U.S. Pat. No. 6,468,302 which is a divisional of application Ser. No. 09/298,063, filed Apr. 22, 1999, which issued as U.S. Pat. No. 6,273,911 on Aug. 14, 2001, the contents of which are hereby incorporated by reference.

BACKGROUND OF THE INVENTION

The present invention relates to expandable endoprosthesis devices, generally known as stents, which are designed for implantation in a patient's body lumen, such as blood vessels to maintain the patency thereof. These devices are particularly useful in the treatment and repair of blood vessels after a stenosis has been compressed by percutaneous transluminal coronary angioplasty (PTCA), percutaneous transluminal angioplasty (PTA), or removed by atherectomy or other means.

Stents are generally cylindrically-shaped devices which function to hold open and sometimes expand a segment of a blood vessel or other lumen such as a coronary artery. They are particularly suitable for use to support the lumen or hold back a dissected arterial lining which can occlude the fluid passageway therethrough.

A variety of devices are known in the art for use as stents and have included coiled wires in a variety of patterns that are expanded after being placed intraluminally on a balloon catheter; helically wound coiled springs manufactured from an expandable heat sensitive metal; and self-expanding stents inserted in a compressed state and shaped in a zigzag pattern. One of the difficulties encountered using prior art stents involved maintaining the radial rigidity needed to hold open a body lumen while at the same time maintaining the longitudinal flexibility of the stent to facilitate its delivery and accommodate the often tortuous path of the body lumen.

Another problem area has been the limited range of expandability. Certain prior art stents expand only to a limited degree due to the uneven stresses created upon the stents during radial expansion. This necessitates providing stents with a variety of diameters, thus increasing the cost of manufacture. Additionally, having a stent with a wider range of expandability allows the physician to redilate the stent if the original vessel size was miscalculated.

Another problem with the prior art stents has been contraction of the stent along its longitudinal axis upon radial expansion of the stent. This can cause placement problems within the artery during expansion.

Various means have been described to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon on the catheter to expand the stent into a permanent expanded condition and then deflating the balloon and removing the catheter.

What has been needed is a stent which not only addresses the aforementioned problems, but also has variable strength, yet maintains flexibility so that it can be readily advanced through tortuous passageways and radially expanded over a wider range of diameters with minimal longitudinal contraction to accommodate a greater range of vessel diameters, all with minimal longitudinal contraction. Certainly, the expanded stent must have adequate structural strength (hoop strength) to hold open the body lumen in which it is expanded. The control of stent strength at specific locations along the stent results in a highly customizable device specifically adapted to the unique body lumen formation in the patient.

One approach to the variable strength problem is to increase strut thickness. This technique is disclosed in co-pending application Ser. No. 08/943,992, filed Oct. 3, 1997, by T. Limon and T. Turnlund, entitled "Stent Having Varied Amounts Of Structural Strength Along Its Length," whose entire contents are hereby incorporated by reference. Another approach is to vary the length or width of the strut at a constant strut thickness. The present invention is directed to this approach.

SUMMARY OF THE INVENTION

The present invention is directed to stents of enhanced longitudinal flexibility and configuration which permit the stents to expand radially to accommodate a greater number of different diameter vessels, both large and small, than heretofore was possible. The stents of the instant application also have greater flexibility along their longitudinal axis to facilitate delivery through tortuous body lumens, but remain highly stable when expanded radially, to maintain the patency of a body lumen such as an artery or other vessel when implanted therein. The unique patterns of the stents of the instant invention permit both greater longitudinal flexibility and enhanced radial expansibility and stability compared to prior art stents.

Each of the different embodiments of stents of the present invention includes a plurality of adjacent cylindrical elements which are generally expandable in the radial direction and arranged in alignment along a longitudinal stent axis. The cylindrical elements are formed in a variety of serpentine wave patterns transverse to the longitudinal axis and contain a plurality of alternating peaks and valleys. At least one interconnecting member extends between adjacent cylindrical elements and connects them to one another. These interconnecting members insure minimal longitudinal contraction during radial expansion of the stent in the body vessel. The serpentine patterns have varying degrees of curvature in the regions of the peaks and valleys and are adapted so that radial expansion of the cylindrical elements are generally uniform around their circumferences during expansion of the stents from their contracted conditions to their expanded conditions.

The resulting stent structures are a series of radially expandable cylindrical elements that are spaced longitudinally close enough so that small dissections in the wall of a body lumen may be pressed back into position against the lumenal wall, but not so close as to compromise the longitudinal flexibility of the stent both when being negotiated through the body lumens in their unexpanded state and when expanded into position. The serpentine patterns allow for an even expansion around the circumference by accounting for the relative differences in stress created by the radial expansion of the cylindrical elements. Each of the individual cylindrical elements may rotate slightly relative to their adjacent cylindrical elements without significant deformation, cumulatively providing stents which are flexible along their length and about their longitudinal axis, but which are still very stable in the radial direction in order to resist collapse after expansion.

Each of the stents of the present invention can be readily delivered to the desired lumenal location by mounting it on an expandable member, such as a balloon, of a delivery catheter and passing the catheter-stent assembly through the body lumen to the implantation site. A variety of means for securing the stents to the expandable member of the catheter for delivery to the desired location are available. It is presently preferred to compress or crimp the stent onto the unexpanded balloon. Other means to secure the stent to the balloon include providing ridges or collars on the inflatable member to restrain lateral movement, using bioabsorbable temporary adhesives, or adding a retractable sheath to cover the stent during delivery through a body lumen.

The presently preferred structures for the expandable cylindrical elements which form the stents of the present invention generally have a circumferential serpentine pattern containing a plurality of alternating peaks and valleys. The degrees of curvature along adjacent peaks and valleys are designed to compensate for the stresses created during expansion of the stent so that expansion of each of the peaks and valleys is uniform relative to one another. This particular structure permits the stents to radially expand from smaller first diameters to any number of larger second diameters since stress is distributed more uniformly along the cylindrical elements. This uniformity in stress distribution reduces the tendency of stress fractures in one particular region and allows high expansion ratios.

The different stent embodiments also allow the stents to expand to various diameters from small to large to accommodate different-sized body lumens, without loss of radial strength and limited contraction of longitudinal length. The open reticulated structure of the stents results in a low mass device. It also enables the perfusion of blood over a large portion of the arterial wall, which can improve the healing and repair of a damaged arterial lining.

The serpentine patterns of the cylindrical elements can have different degrees of curvature of adjacent peaks and valleys to compensate for the expansive properties of the peaks and valleys. Additionally, the degree of curvature along the peaks can be set to be different in immediately adjacent areas to compensate for the expansive properties of the valleys adjacent to it. The more even radial expansion of this design results in stents which can be expanded to accommodate larger diameters with minimal out of plane twisting since the high stresses are not concentrated in any one particular region of the pattern, but are more evenly distributed among the peaks and valleys, allowing them to expand uniformly. Reducing the amount of out of plane twisting also minimizes the potential for thrombus formation.

The serpentine pattern of the individual cylindrical elements can optionally be in phase which each other in order to reduce contraction of the stents along their length when expanded. The cylindrical elements of the stents are plastically deformed when expanded (except with NiTi alloys) so that the stents will remain in the expanded condition and therefore they must be sufficiently rigid when expanded to prevent the collapse thereof in use.

With stents formed from super-elastic nickel-titanium (NiTi) alloys, the expansion occurs when the stress of compression is removed. This allows the phase transformation from martensite back to austenite to occur, and as a result the stent expands.

After the stents are expanded, some of the peaks and/or valleys may, but not necessarily, tip outwardly and embed in the vessel wall. Thus, after expansion, the stents might not have a smooth outer wall surface. Rather, they might have small projections which embed in the vessel wall and aid in retaining the stents in place in the vessel. The tips projecting outwardly and strut twisting are due primarily to the struts having a high aspect ratio. In one preferred embodiment, the strut width is about 0.0035 inch and a thickness of about 0.0022 inch, providing an aspect ratio of 1.6. An aspect ratio of 1.0 will produce less tipping and twisting.

The elongated interconnecting members which interconnect adjacent cylindrical elements should have a transverse cross-section similar to the transverse dimensions of the undulating components of the expandable cylindrical elements. The interconnecting members may be formed in a unitary structure with the expandable cylindrical elements formed from the same intermediate product, such as a tubular element, or they may be formed independently and mechanically secured between the expandable cylindrical elements.

Preferably, the number and location of the interconnecting members can be varied in order to develop the desired longitudinal flexibility in the stent structure both in the unexpanded as well as the expanded condition. These properties are important to minimize alteration of the natural physiology of the body lumen into which the stent is implanted and to maintain the compliance of the body lumen which is internally supported by the stent. Generally, the greater the longitudinal flexibility of the stents, the easier and the more safely they can be delivered to the implantation site, especially where the implantation site is on a curved section of a body lumen, such as a coronary artery or a peripheral blood vessel, and especially saphenous veins and larger vessels.

Following from the foregoing proposition is that, in general, the more interconnecting members there are between adjacent cylindrical elements of the stent, the less longitudinal flexibility there is. More interconnecting members reduces flexibility, but also increases the coverage of the vessel wall, which helps prevent tissue prolapse between the stent struts. Such an approach to stent design is disclosed in co-pending patent application Ser. No. 09/008,366, filed Jan. 16, 1999, by Daniel L. Cox, entitled "Flexible Stent And Method of Use," whose entire contents are hereby incorporated by reference.

The present invention in particular relates to the control of stent strength by varying the strut geometry along the length of the stent. By making the stent stronger or weaker in different regions of the stent, the properties can be customized to a particular application. The stent properties that could be altered include, but are not limited to, the width of each strut, and/or the length of each cylindrical element or ring at a constant strut thickness.

The variation of the strength of the stent affects the manner in which the stent expands. As expected, the wider struts tend not to deform as easily as the narrower struts during expansion, while the longer struts within the longer cylindrical elements are better adapted to deployment in larger diameter vessels. On the other hand, an area with shorter cylindrical elements tends to have greater radial strength than an area with longer cylindrical elements, given the same strut cross-sectional area.

In a preferred embodiment, the present invention is directed to a longitudinally flexible stent for implanting in a body lumen and which is expandable from a contracted condition to an expanded condition. The present invention stent preferably comprises a plurality of adjacent cylindrical elements, each cylindrical element having a circumference extending around a longitudinal stent axis, being substantially independently expandable in the radial direction, wherein the plurality of adjacent cylindrical elements are arranged in alignment along the longitudinal stent axis and define a first end section, a second end section, and a center section therebetween; each cylindrical element having struts of a constant thickness formed in a generally serpentine wave pattern transverse to the longitudinal axis and containing alternating valley portions and peak portions; a plurality of interconnecting members extending between the adjacent cylindrical elements and connecting valley portions of adjacent cylindrical elements to one another; and wherein the struts of at least one cylindrical element has greater mass than the struts in other cylindrical elements.

The greater mass strut is achieved by increasing the length of the strut, and/or increasing the width of the strut. On the other hand, the greater mass strut is not achieved by increasing strut thickness.

In an exemplary embodiment, the present invention stent has struts in the cylindrical elements in the center section that have a greater mass than the struts in the cylindrical elements in the first end section and the second end section. The greater mass is achieved by increasing strut width and/or increasing strut length.

In another exemplary embodiment, the present invention stent has struts in the cylindrical elements in the center section and the second end section that have a greater mass than the struts in the cylindrical elements in the first end section. The greater mass struts is achieved by increasing strut width and/or increasing strut length.

Still another exemplary embodiment of the present invention stent includes struts in the first end section and the second end section having greater mass than the struts in the cylindrical elements in the center section. The greater mass struts is achieved by increasing strut width and/or increasing strut length.

Increasing or decreasing strut length in each section changes the moment arm and consequently the radial strength of that section. Increasing or decreasing strut width at a constant strut thickness changes the cross-sectional area of the strut and the bending moment. Hence, a wider strut has greater hoop strength and is more resistant to bending.

Other features and advantages of the present invention will become more apparent from the following detailed description of the invention, when taken in conjunction with the accompanying exemplary drawings.

BRIEF DESCRIPTION OF THE DRAWINGS

FIG. 1 is an elevational view, partially in section, depicting the stent embodying features of the present invention mounted on a delivery catheter disposed within a vessel.

FIG. 2 is an elevational view, partially in section, similar to that shown in FIG. 1, wherein the stent is expanded within a vessel, pressing the lining against the vessel wall.

FIG. 3 is an elevational view, partially in section, showing the expanded stent within the vessel after withdrawal of the delivery catheter.

FIG. 6 is a plan view of an alternative embodiment flattened stent of the present invention, which illustrates increased width of the struts in a center section in between the first and second end sections.

FIG. 7 is a plan view of an alternative embodiment flattened stent of the present invention, which illustrates increased length of the cylindrical elements at the center and second end sections.

FIG. 8 is a plan view of a preferred embodiment flattened stent of the present invention, which illustrates increased strut width at the end sections.

DETAILED DESCRIPTION OF THE PREFERRED EMBODIMENTS

Figure 5:
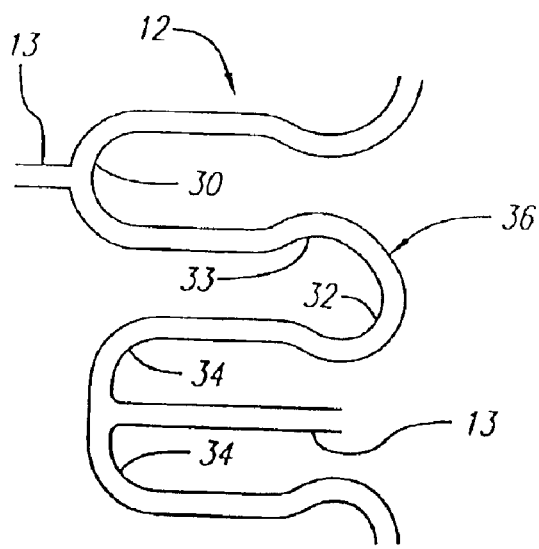
FIG. 5 is an enlarged partial view of an alternative embodiment stent depicting the serpentine pattern with varying diameters at the peaks and valleys.

Prior art stent designs, such as the MultiLink Stent™ manufactured by Advanced Cardiovascular Systems, Inc., Santa Clara, Calif., include a plurality of cylindrical rings that are connected by three connecting members between adjacent cylindrical rings. Each of the cylindrical rings is formed of a repeating pattern of U-, Y-, and W-shaped members, typically having three repeating patterns forming each cylindrical ring. A more detailed discussion of the configuration of the MultiLink Stent™ can be found in U.S. Pat. No. 5,569,295 (Lam) and U.S. Pat. No. 5,514,154 (Lau et al.), whose contents are hereby incorporated by reference.

Beyond those prior art stents, FIG. 1 illustrates an exemplary embodiment of stent 10 incorporating features of the present invention, which stent is mounted onto delivery catheter 11. Stent 10 generally comprises a plurality of radially expandable cylindrical elements 12 disposed generally coaxially and interconnected by interconnecting members 13 disposed between adjacent cylindrical elements 12. The delivery catheter 11 has an expandable portion or balloon 14 for expanding stent 10 within artery 15 or other vessel. The artery 15, as shown in FIG. 1, has a dissected or detached lining 16 which has occluded a portion of the arterial passageway.

The delivery catheter 11 onto which stent 10 is mounted is essentially the same as a conventional balloon dilatation catheter for angioplasty procedures. The balloon 14 may be formed of suitable materials such as polyethylene, polyethylene terephthalate, polyvinyl chloride, nylon and, ionomers such as Surlyn® manufactured by the Polymer Products Division of the Du Pont Company. Other polymers may also be used.

In order for stent 10 to remain in place on balloon 14 during delivery to the site of the damage within artery 15, stent 10 is compressed or crimped onto balloon 14. A retractable protective delivery sleeve 20 may be provided to ensure that stent 10 stays in place on balloon 14 of delivery catheter 11 and to prevent abrasion of the body lumen by the open surface of stent 10 during delivery to the desired arterial location. Other means for securing stent 10 onto balloon 14 also may be used, such as providing collars or ridges on the ends of the working portion, i.e., the cylindrical portion, of balloon 14. Each radially expandable cylindrical element 12 of stent 10 may be independently expanded. Therefore, balloon 14 may be provided with an inflated shape other than cylindrical, e.g., tapered, to facilitate implantation of stent 10 in a variety of body lumen shapes.

In a preferred embodiment, the delivery of stent 10 is accomplished in the following manner. Stent 10 is first mounted onto inflatable balloon 14 on the distal extremity of delivery catheter 11. Stent 10 may be crimped down onto balloon 14 to obtain a low profile. The catheter-stent assembly can be introduced within the patient's vasculature in a conventional Seldinger technique through a sliding catheter (not shown). Guidewire 18 is disposed through the damaged arterial section with the detached or dissected lining 16. The catheter-stent assembly is then advanced over guide wire 18 within artery 15 until stent 10 is directly under detached lining 16. Balloon 14 of catheter 11 is inflated or expanded, thus expanding stent 10 against the inside of artery 15, which is illustrated in FIG. 2. While not shown in the drawing, artery 15 is preferably expanded slightly by the expansion of stent 10 to seat or otherwise embed stent 10 to prevent movement. Indeed, in some circumstances during the treatment of stenotic portions of an artery, the artery may have to be expanded considerably in order to facilitate passage of blood or other fluid therethrough.

While FIGS. 1–3 depict a vessel having detached lining 16, stent 10 can be used for purposes other than repairing the lining. Those other purposes include, for example, supporting the vessel, reducing the likelihood of restenosis, or assisting in the attachment of a vascular graft (not shown) when repairing an aortic abdominal aneurysm.

In general, stent 10 serves to hold open artery 15 after catheter 11 is withdrawn, as illustrated in FIG. 3. Due to the formation of stent 10 from an elongated tubular member, the undulating component of the cylindrical elements of stent 10 is relatively flat in a transverse cross-section so that when stent 10 is expanded, cylindrical elements 12 are pressed into the wall of artery 15 and as a result do not interfere with the blood flow through artery 15. Cylindrical elements 12 of stent 10 that are pressed into the wall of artery 15 will eventually be covered with endothelial cell growth that further minimizes blood flow turbulence. The serpentine pattern of cylindrical sections 12 provide good tacking characteristics to prevent stent movement within the artery. Furthermore, the closely spaced cylindrical elements 12 at regular intervals provide uniform support for the wall of artery 15, and consequently are well adapted to tack up and hold in place small flaps or dissections in the wall of artery 15 as illustrated in FIGS. 2 and 3.

The stresses involved during expansion from a low profile to an expanded profile are generally evenly distributed among the various peaks and valleys of stent 10. As seen in the perspective view of FIG. 4, each expanded cylindrical element 12 of stent 10 embodies the serpentine pattern having a plurality of peaks 36 and valleys 30 that aid in the even distribution of expansion forces. In this exemplary embodiment, interconnecting members 13 serve to connect adjacent valleys 30 of each adjacent cylindrical element 12 as described above. The various peaks and valleys generally have U, Y, and W shapes, in a repeating pattern to form each cylindrical element 12.

During expansion, double-curved portions (W) 34 located in the region of the valley where interconnecting members 13 are connected have the most mass and accordingly are the stiffest structure during deformation. In contrast, peak portions (U) 36 are the least stiff, and valley portions (Y) 30 have an intermediate stiffness.

By allocating the amount of mass to specific struts, it is possible to create a stent having variable strength with greater strength at the high mass areas. Given a stent having a constant thickness in its struts, the increased mass is accomplished by increasing the width of the strut and/or increasing the length of the strut. The following exemplary embodiments apply this theory.

FIG. 6 is a plan view of exemplary embodiment stent 10 with the structure flattened out into two dimensions to facilitate explanation. Stent 10 can be viewed in FIG. 6 as having three sections; namely, first and second end sections 31A and 31B, respectively, and center section 31C. As is shown, first end section 31A has interconnecting members 13 in each double-curved portion (W) 34, thereby providing maximum support at that end of the stent. First end section 31A may optionally have connected thereto center section 31C as shown. But in an alternative embodiment (not shown), center section 31C may have the same number of interconnecting members 13 with the same cylindrical element design as first end section 31A or second end section 31B. One may therefore think of this alternative embodiment as having center section 31C completely omitted.

The FIG. 6 embodiment incorporates stent strut 17 in each cylindrical element 12 at first end section 31A and second end section 31B that have a narrow width as compared to the broader or wider strut width of stent strut 19 in center section 31B. As explained earlier, this construction can be viewed from a mass-based approach. In particular, at a constant strut thickness and with the presence of wider struts 19, each cylindrical element 12 in center section 31C has a greater mass than the cylindrical elements in either the first or second end sections 31A, 31B.

The wider struts 19 concentrate more radial or hoop strength at the center of stent 10. This design is especially well suited to a very focal lesion in which a gradual transition to the normal artery is desired.

In the exemplary embodiment of FIG. 6, each cylindrical element 12 in center section 31C includes preferably three interconnecting members 13 to connect double curved portion (W) 34 of one cylindrical element 12 to valley portion (Y) 30 of an adjacent cylindrical element 12. In the exemplary embodiment shown in FIG. 6, interconnecting members 13 within center section 42 are preferably spaced 120 degrees apart.

Each cylindrical element 12 is made up of three repeating serpentine wave pattern sections with valley portion (Y) 30, peak portion (U) 36, and double curved portion (W) 34. Valley portion 30 and peak portion 36 each has a generally single radius of curvature. Valley portion 30 is connected to interconnecting member 13 and bridges to, peak portion 36. Interconnecting members 13 are preferably straight. All of the aforementioned structures preferably lie within center section 31C. The cylindrical clement construction is repeated for first and second end sections 31A and 31B.

Cylindrical element 12 found within second end section 31B has repeating serpentine wave patterns with valley portion (Y) 30 and peak portion (U) 36, but no double curve portion (W) 34. Of course, the difference is the omission of interconnecting members 13 in second end section 31B to connect the cylindrical elements to yet another adjacent cylindrical element. Although contemplated but not shown, there can be more than one cylindrical element 12 in second end section 31B.

Interconnecting members 13 may be aligned axially in every other cylindrical element 12, as shown in FIG. 6, or they may be staggered depending on the design's bending requirements. Indeed, the present invention controls stent flexibility by using the number of interconnecting members between cylindrical elements of the stents. Generally speaking, the more interconnecting members there are between cylindrical elements of the stent, the less longitudinal flexibility there is. So more interconnecting members reduces flexibility, but increases the coverage of the vessel wall which helps prevent tissue prolapse between the stent struts.

In summary, it is contemplated that the number of cylindrical elements within first and second end sections 31A, 31B, and center section 31C be varied as needed. The numbers and locations of interconnecting members 13 may be varied as needed too.

In a preferred embodiment stent 50, shown in a flattened, plan view of FIG. 8, the opposite to the stent design shown in FIG. 6 could be applied. Here, center section 52C has narrow struts 54 and wider struts 56 are found in first end section 52A and second end section 52B.

This preferred embodiment stent 50 could be used to give extra support or radial strength at the ends of the stent since the ends are not supported by an adjacent cylindrical element. Favoring such an approach are some existing balloon expandable stent designs that start expanded at the ends of the stent before the center when deployed. If modified in accordance with the preferred embodiment, such stents would expand more consistently or homogeneously along the length of the stent.

Aside from strut widths, the overall strut pattern of stent 50 in FIG. 8 is similar to the embodiment shown in FIG. 6. Stent 50 is formed from individual rings or cylindrical element 58 that are linked by interconnecting members 60. Each ring or cylindrical element 58 is comprised of a serpentine wave pattern made up of valley portions (Y's) 62, double curved portions (W's) 64, and peak portion (U's) 66. Interconnecting member 60 preferably joins valley portion (Y) 62 of one cylindrical element 58 to double curved portion (W) 64 of the adjacent cylindrical element 58. There are preferably three interconnecting members 60 spaced 120 degrees apart and joining each pair of adjacent cylindrical elements 58. Of course, the number and locations of interconnecting members 60 joining cylindrical elements 58 can be changed as required.

In the preferred embodiment, peak portion (U) 66 has optional strut segment 68 shaped like a loop or bulb. Strut segment 68 may have a constant or variable curvature to affect expansion stresses and uniformity, the details of which are explained below in connection with FIG. 5.

FIG. 7 is a plan view of alternative embodiment stent 21 flattened into a two-dimensional plane for the sake of illustration. Again from a mass based approach, the present invention stent 21 has struts 22 in the cylindrical elements in center section 23C and second end section 23B that have a greater mass than struts 24 in the cylindrical elements in first end section 23A. Looking at the exemplary embodiment of FIG. 7 a bit differently, the drawing also depicts the present invention stent 21 including struts 22 in the cylindrical elements in center section 23C having the same mass and general shape as struts 22 in the cylindrical elements in second end section 23B.

To achieve the greater mass at a constant thickness, struts in each cylindrical element in center section 23C have a greater length than the struts in the cylindrical elements in first end section 23A. Alternatively, struts in each cylindrical element in center section 23C and second end section 23B preferably have a greater length than the struts in the cylindrical element in first end section 23A. As such, each cylindrical element in center section 23C or in second end section 23B has a greater mass than a cylindrical element in first end section 23A.

The embodiment of FIG. 7 uses the strut length to control the radial strength of stent 21. The struts in cylindrical elements in first end section 23A are shorter with a shorter moment arm and therefore stronger than the long struts in center section 23C or second end section 23B. In effect, the radial strength of stent 10 is reduced by the increased moment arm in sections 23C and 23B.

Such a design could be used for ostial lesions in which the region at the ostium requires more strength than the area away from the ostium. The present invention stent in a balloon expandable embodiment is also well suited for use in saphenous vein grafts, because the distal end of stent 21 would open first and trap any plaque from flowing downstream.

The arrangement of the interconnecting members 13, and the repeating serpentine wave patterns with valley portion (Y) 30, peak portion (U) 36, and double curve portion (W) 34 is similar to the embodiment shown in FIG. 6. Naturally, there can be more or fewer cylindrical elements 12 than that shown in first and second end sections 23A, 23B and center section 23C. The number and locations of interconnecting members 13 can also be varied as needed to adjust longitudinal rigidity of stent 21.

Figure 8A:
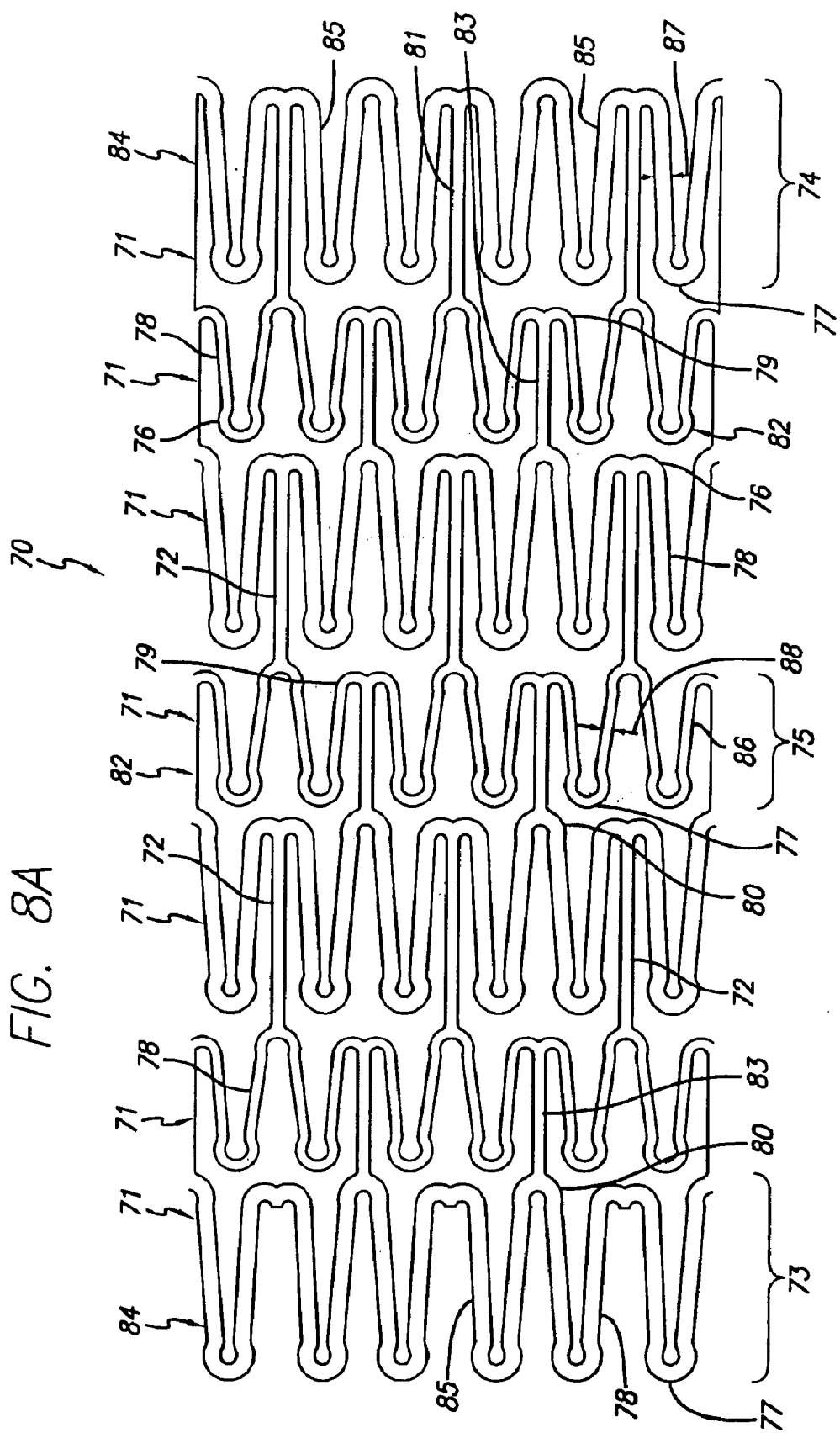
FIG. 8A is a plan view of an alternative embodiment flattened stent of the present invention, depicting alternating long and short cylindrical elements and straight portions with relatively wider and narrower portions.

In an alternative embodiment as shown in FIG. 8A, the increased strut length concept of FIG. 7 can be incorporated into the strut pattern shown in FIG. 8. In such a stent, the first and second high mass ends have long struts for reduced radial or hoop strength while the center section has shorter length struts. As used herein, cylindrical elements and rings are used interchangeably, interconnecting members and links are used interchangeably, and center section and third section are used interchangeably. Referring to the embodiment of FIG. 8A, an unexpanded stent 70 is formed of rings or cylindrical elements 71 which are connected by links or interconnecting members 72. The cylindrical elements are arranged in a first end section 73, a second end section 74, and a center section 75. Each of the cylindrical elements is formed in a generally serpentine wave pattern 76 as shown in FIG. 8A, and the curved portions of the wave pattern are connected by generally straight portions 78. Each cylindrical element has at least one U-shaped member 77. As with the other embodiments, a W-shaped member 79 is formed by at least one of the cylindrical elements and one of the interconnecting members, and a Y-shaped member 80 is formed by at least one of the cylindrical elements and one of the interconnecting members. In this embodiment shown in a flattened configuration, the cylindrical elements are connected together and arranged along the longitudinal stent axis. In tubular form, each cylindrical element has a circumference extending around the longitudinal stent axis. In FIG. 8A, the interconnecting members extend substantially parallel to the longitudinal stent axis. As can be seen, interconnecting members 81 have a length that is longer than cylindrical elements 82. Similarly, interconnecting members 83 have a length that is shorter than cylindrical elements 84. The generally straight portions of the cylindrical element in the first end section 73 or the second end section 74 has a length 85 that is longer than the length 86 of generally straight portions of the cylindrical element in the center section 75. Longitudinal flexibility is achieved at least in part by varying the widths of the various portions of the cylindrical elements. For example, the generally straight portions 87 in the first end section or the second end section are wider than the generally straight portions 88 in the center section.

Figure 4:
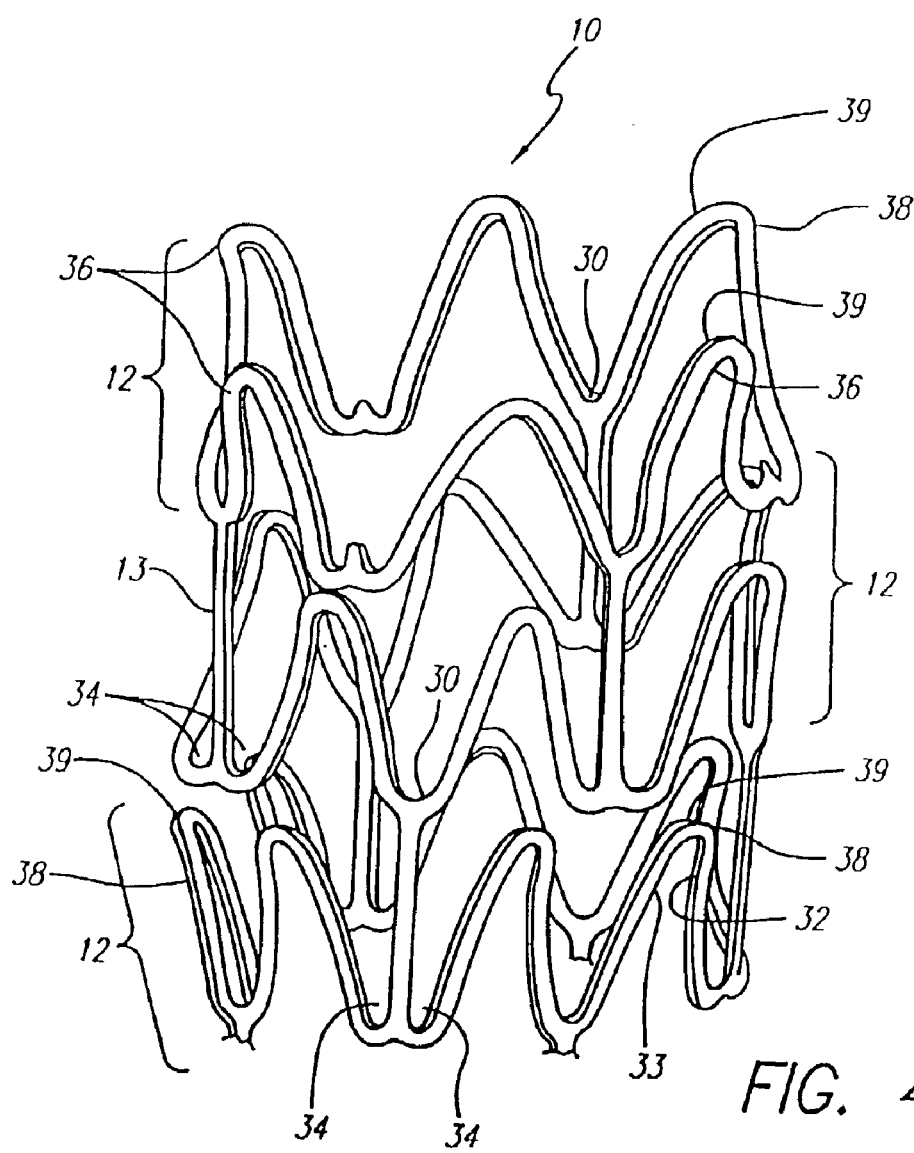
FIG. 4 is a perspective view of the stent in FIGS. 1–3 in the expanded state.

As best seen in FIG. 4, because of the mass involved with the present invention stent designs, double curved portion (W) 34 is the stiffest structure and peak portion 36 is the least stiff structure, which account for the different stresses arising during expansion. Also, the least stiff structure, peak portion 36, is positioned between double curved portion 34 and valley portion 30, which are comparatively stiffer structures.

To even out the stresses, peak portion 36 in an alternative embodiment optionally has different curvatures at regions 32 and 33, as seen in FIG. 5. Region 33 has a larger radius than region 32 and expands more easily. Since region 32 is adjacent the stiffer area of double curved portion 34, both region 32 and double curved portion 34 expand more uniformly and more evenly distribute the expansion stresses. Further, valley portion 30 and double curved portion 34 have different diameters to even out the expansion forces in relation to peak portion 36. Due to the unique structure as described, the shortcomings of the prior art, which include out of plane twisting of the metal, are avoided. These differing degrees of curvature along peak portion 36 allow for the more even expansion of the cylindrical element 12 as a whole.

Stent 10 of FIGS. 1–6 has an expansion ratio from the crimped to expanded configuration in the range of about, for example, 1.0 to 5.0, while maintaining structural integrity when expanded. As depicted in FIG. 4, after expansion of stent 10, portions of the various cylindrical elements 12 may turn outwardly, forming small projections 38 that embed in the vessel wall. More precisely, tip 39 of peak portion 36 tilts outwardly a sufficient amount upon expansion of stent 10 to embed into the vessel wall thus helping secure implanted stent 10. Upon expansion, projections 38 create an outer wall surface on stent 10 that is not smooth. On the other hand, while projections 38 assist in securing stent 10 in the vessel-wall, they are not sharp so as to cause trauma or damage to the vessel wall.

Tips 39 projecting outwardly and strut twisting are due primarily to the struts having a high aspect ratio. In one preferred embodiment, the strut width is about 0.0035 inch and a thickness of about 0.0022 inch, providing an aspect ratio of 1.6. An aspect ratio of 1.0 will produce less tipping and twisting.

The dimensions of any of the foregoing exemplary embodiments can be selected to achieve optimal expansion and strength characteristics for a given stent. The number of bends in each cylindrical element, as shown in FIGS. 6, 7 and 8 for example, can also be varied.

In many of the drawing figures, the present invention stent is depicted flat, in a plan view for ease of illustration. All of the embodiments depicted herein are cylindrically-shaped stents that are generally formed from tubing by laser cutting as described below.

One important feature of all of the embodiments of the present invention is the capability of the stents to expand from a low-profile diameter to a diameter much greater than heretofore was available, while still maintaining structural integrity in the expanded state and remaining highly flexible. Due to the novel structures, the stents of the present invention each have an overall expansion ratio of about 1.0 up to about 4.0 times the original diameter, or more, using certain compositions of stainless steel. For example, a 316L stainless steel stent of the invention can be radially expanded from a diameter of 1.0 unit up to a diameter of about 4.0 units, which deforms the structural members beyond the elastic limit. The stents still retain structural integrity in the expanded state and will serve to hold open the vessel in which they are implanted. Materials other than stainless steel (316L) may afford higher or lower expansion ratios without sacrificing structural integrity.

The stents of the present invention can be made in many ways. However, the preferred method of making the stent is to cut a thin-walled tubular member, such as stainless steel tubing to remove portions of the tubing in the desired pattern for the stent, leaving relatively untouched the portions of the metallic tubing which are to form the stent. It is preferred to cut the tubing in the desired pattern by means of a machine-controlled laser.

The tubing may be made of suitable biocompatible material such as stainless steel. The stainless steel tube may be alloy-type: 316L SS, Special Chemistry per ASTM F138-92 or ASTM F139-92 grade 2. Special Chemistry of type 316L per ASTM F138-92 or ASTM F139-92 Stainless Steel for Surgical Implants in weight percent.

| | |
|---|---|
| Carbon (C) | 0.03% max. |
| Manganese (Mn) | 2.00% max. |
| Phosphorous (P) | .025% max. |
| Sulphur (S) | 0.010% max. |
| Silicon (Si) | 0.75% max. |
| Chromium (Cr) | 17.00–19.00% |
| Nickel (Ni) | 13.00–15.50% |
| Molybdenum (Mo) | 2.00–3.00% |
| Nitrogen (N) | 0.10% max. |
| Copper (Cu) | 0.50% max. |
| Iron (Fe) | Balance |

The stent diameter is very small, so the tubing from which it is made must necessarily also have a small diameter. Typically the stent has an outer diameter on the order of about 0.06 inch in the unexpanded condition, the same outer diameter of the tubing from which it is made, and can be expanded to an outer diameter of 0.2 inch or more. The wall thickness of the tubing is about 0.003 inch.

Generally, the tubing is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished stent.

The process of cutting a pattern for the stent into the tubing generally is automated except for loading and unloading the length of tubing. For example, a pattern can be cut in tubing using a CNC-opposing collet fixture for axial rotation of the length of tubing, in conjunction with CNC X/Y table to move the length of tubing axially relative to a machine-controlled laser as described. The entire space between collets can be patterned using the $CO_2$, Nd or YAG laser set-up of the foregoing example. The program for control of the apparatus is dependent on the particular configuration used and the pattern to be ablated in the coding.

Cutting a fine structure (0.0034 inch web width) requires minimal heat input and the ability to manipulate the tube with precision. It is also necessary to support the tube yet not allow the stent structure to distort during the cutting operation. In order to successfully achieve the desired end results, the entire system must be configured very carefully. The tubes are made of stainless steel with an outside diameter of 0.060 inch to 0.100 inch and a wall thickness of 0.002 inch to 0.008 inch. These tubes are fixtured under a laser and positioned utilizing a CNC to generate a very intricate and precise pattern. Due to the thin wall and the small geometry of the stent pattern (0.0035 inch typical strut width), it is necessary to have very precise control of the laser, its power level, the focused spot size, and the precise positioning of the laser cutting path.

In order to minimize the heat input into the stent structure, which prevents thermal distortion, uncontrolled burn out of the metal, and metallurgical damage due to excessive heat, and thereby produce a smooth debris-free cut, a Q-switched Nd/YAG, typically available from Quantonix of Hauppauge, N.Y., that is frequency-doubled to produce a green beam at 532 nanometers is utilized. Q-switching produces very short pulses (<100 nS) of high peak powers (kilowatts), low energy per pulse ($\leq 3$ mJ), at high pulse rates (up to 40 kHz). The frequency doubling of the beam from 1.06 microns to 0.532 microns allows the beam to be focused to a spot size that is two times smaller, therefore increasing the power density by a factor of four times. With all of these parameters, it is possible to make smooth, narrow cuts in the stainless steel tubes in very fine geometries without damaging the narrow struts that make up the stent structure. Hence, the system of the present invention makes it possible to adjust the laser parameters to cut narrow kerf width which will minimize the heat input into the material.

The positioning of the tubular structure requires the use of precision CNC equipment such as that manufactured and sold by Anorad Corporation. In addition, a unique rotary mechanism has been provided that allows the computer program to be written as if the pattern were being cut from a flat sheet. This allows both circular and linear interpolation to be utilized in programming.

The optical system which expands the original laser beam, delivers the beam through a viewing head and focuses the beam onto the surface of the tube, incorporates a coaxial gas jet and nozzle that helps to remove debris from the kerf and cools the region where the beam interacts with the material as the beam cuts and vaporizes the metal. It is also necessary to block the beam as it cuts through the top surface of the tube and prevent the beam, along with the molten metal and debris from the cut, from impinging on the opposite surface of the tube.

In addition to the laser and the CNC positioning equipment, the optical delivery system includes a beam expander to increase the laser beam diameter, a circular polarizer, typically in the form of a quarter wave plate, to eliminate polarization effects in metal cutting, provisions for a spatial filter, a binocular viewing head and focusing lens, and a coaxial gas jet that provides for the introduction of a gas stream that surrounds the focused beam and is directed along the beam axis. The coaxial gas jet nozzle (0.018 inch I.D.) is centered around the focused beam with approximately 0.010 inch between the tip of the nozzle and the tubing. The jet is pressurized with oxygen at 20 psi and is directed at the tube with the focused laser beam exiting the tip of the nozzle (0.018 inch dia.). The oxygen reacts with the metal to assist in the cutting process very similar to oxyacetylene cutting. The focused laser beam acts as an ignition source and controls the reaction of the oxygen with the metal. In this manner, it is possible to cut the material with a very fine kerf with precision.

In order to prevent burning by the beam and/or molten slag on the far wall of the tube I.D., a stainless steel mandrel (approx. 0.034 inch dia.) is placed inside the tube and is allowed to roll on the bottom of the tube as the pattern is cut. This acts as a beam/debris barrier protecting the far wall I.D.

Alternatively, this may be accomplished by inserting a second tube inside the stent tube which has an opening to trap the excess energy in the beam which is transmitted through the kerf along which collecting the debris that is ejected from the laser cut kerf. A vacuum or positive pressure can be placed in this shielding tube to remove the collection of debris.

Another technique that could be utilized to remove the debris from the kerf and cool the surrounding material would be to use the inner beam blocking tube as an internal gas jet. By sealing one end of the tube and making a small hole in the side and placing it directly under the focused laser beam, gas pressure could be applied creating a small jet that would force the debris out of the laser cut kerf from the inside out. This would eliminate any debris from forming or collecting on the inside of the stent structure. It would place all the debris on the outside. With the use of special protective coatings, the resultant debris can be easily removed.

In most cases, the gas utilized in the jets may be reactive or non-reactive (inert). In the case of reactive gas, oxygen or compressed air is used. Oxygen is used in this application since it offers more control of the material removed and reduces the thermal effects of the material itself. Inert gas such as argon, helium, or nitrogen can be used to eliminate any oxidation of the cut material. The result is a cut edge with no oxidation, but there, is usually a tail of molten material that collects along the exit side of the gas jet that must be mechanically or chemically removed after the cutting operation.

The cutting process utilizing oxygen with the finely focused green beam results in a very narrow kerf (approximately 0.0005 inch) with the molten slag re-solidifying along the cut. This traps the cut-out scrap of the pattern requiring further processing. In order to remove the slag debris from the cut allowing the scrap to be removed from the remaining stent pattern, it is necessary to soak the cut tube in a solution of HCL for approximately eight minutes at a temperature of approximately 55 degrees C. Before it is soaked, the tube is placed in a bath of alcohol/water solution and ultrasonically cleaned for approximately one minute to remove the loose debris left from the cutting operation. After soaking, the tube is ultrasonically cleaned in the heated HCL for one to four minutes depending upon the wall thickness. To prevent cracking/breaking of the struts attached to the material left at the two ends of the stent pattern due to harmonic oscillations induced by the ultrasonic cleaner, a mandrel is placed down the center of the tube during the cleaning/scrap removal process. At completion of this process, the stent structures are rinsed in water. They are now ready for electropolishing.

The stents are preferably electrochemically polished in an acidic aqueous solution such as a solution of ELECTRO-GLO #300, sold by the ELECTRO-GLO Co., Inc. in Chicago, Ill., which is a mixture of sulfuric acid, carboxylic acids, phosphates, corrosion inhibitors and a biodegradable surface active agent. The bath temperature is maintained at about 110–133 degrees F. and the current density is about 0.4 to about 1.5 amps per in$^2$. Cathode to anode area should be at least about two to one. The stents may be further treated if desired, for example by applying a biocompatible coating.

Direct laser cutting produces edges which are essentially perpendicular to the axis of the laser cutting beam, in contrast with chemical etching and the like which produce pattern edges which are angled. Hence, the laser cutting process of the present invention essentially provides stent cross-sections, from cut-to-cut, which are square or rectangular, rather than trapezoidal. The resulting stent structure provides superior performance.

The stent tubing may be made of suitable biocompatible material such as stainless steel, titanium, tantalum, superelastic (nickel-titanium) NiTi alloys and even high strength thermoplastic polymers. The stent diameters are very small, so the tubing from which it is made must necessarily also have a small diameter. For PCTA applications, typically the stent has an outer diameter on the order of about 1.65 mm (0.065 inches) in the unexpanded condition, the same outer diameter of the hypotubing from which it is made, and can be expanded to an outer diameter of 5.08 mm (0.2 inches) or more. The wall thickness of the tubing is about 0.076 mm (0.003 inches). For stents implanted in other body lumens, such as PTA applications, the dimensions of the tubing are correspondingly larger. While it is preferred that the stents be made from laser cut tubing, those skilled in the art will realize that the stent can be laser cut from a flat sheet and then rolled up in a cylindrical configuration with the longitudinal edges welded to form a cylindrical member.

In the instance when the stents are made from plastic, the implanted stent may have to be heated within the arterial site where the stents are expanded to facilitate the expansion of the stent. Once expanded, it would then be cooled to retain its expanded state. The stent may be conveniently heated by heating the fluid within the balloon or the balloon itself directly by a known method.

The stents may also be made of materials such as superelastic (sometimes called pseudo-elastic) nickel-titanium (NiTi) alloys. In this case the stent would be formed full size but deformed (e.g. compressed) to a smaller diameter onto the balloon of the delivery catheter to facilitate intraluminal delivery to a desired intraluminal site. The stress induced by the deformation transforms the stent from an austenite phase to a martensite phase, and upon release of the force when the stent reaches the desired intraluminal location, allows the stent to expand due to the transformation back to the more stable austenite phase. Further details of how NiTi superelastic alloys operate can be found in U.S. Pat. No. 4,665,906 (Jervis) and U.S. Pat. No. 5,067,957 (Jervis), incorporated herein by reference in their entirety.

While the invention has been illustrated and described herein in terms of its use as intravascular stents, it will be apparent to those skilled in the art that the stents can be used in other instances in all vessels in the body. Since the stents of the present invention have the novel feature of expanding to very large diameters while retaining their structural integrity, they are particularly well suited for implantation in almost any vessel where such devices are used. This feature, coupled with limited longitudinal contraction of the stent when they are radially expanded, provide a highly desirable support member for all vessels in the body. Other modifications and improvements may be made without departing from the scope of the invention.

What is claimed is:

1. A longitudinally flexible stent for implanting in a body lumen and expandable from a contracted condition to an expanded condition, comprising:

a plurality of adjacent cylindrical elements, each cylindrical element having a circumference extending around a longitudinal stent axis, being substantially independently expandable in the radial direction, wherein the plurality of adjacent cylindrical elements are arranged in alignment along the longitudinal stent axis and define a first end section, a second end section, and a center section therebetween;

each cylindrical element having struts having a constant thickness formed in a generally serpentine wave pattern transverse to the longitudinal axis and containing alternating valley portions and peak portions;

a plurality of interconnecting members extending between the adjacent cylindrical elements and connecting the adjacent cylindrical elements to one another; and wherein the struts of the cylindrical element in the first end section have a greater mass through a longer strut length and a wider strut width than the struts of the cylindrical element in the center section.

2. The stent of claim 1, wherein the struts of the cylindrical element in the second end section have a greater mass than the struts of the cylindrical element in the center section.

3. The stent of claim 1, wherein the struts in the first end section and the second end section have greater strut widths than the struts in the cylindrical element in the center section.

4. A method for constructing a longitudinally flexible stent for implanting in a body lumen and expandable from a contracted condition to an expanded condition, the method comprising the steps of:

providing a plurality of adjacent cylindrical elements, each cylindrical element having a circumference extending around a longitudinal stent axis, being substantially independently expandable in the radial direction;

arranging the plurality of adjacent cylindrical elements in alignment along the longitudinal stent axis to include a first end section, a second end section, and a center section therebetween;

forming struts of constant thickness in each cylindrical element in a generally serpentine wave pattern transverse to the longitudinal axis and containing alternating valley portions and peak portions;

providing a plurality of interconnecting members extending between the adjacent cylindrical elements and connecting the adjacent cylindrical elements to one another; and providing struts of the cylindrical element in the first end section that have a greater mass through a greater strut length and a greater strut width than the struts of the cylindrical element in the center section.

5. The method of claim 4, wherein the method further comprises providing struts of the cylindrical elements in the first end section and the second end section having a greater strut width than the struts of the cylindrical elements in the center section.

6. The method of claim 4, wherein the method further comprises providing struts of the cylindrical elements in the first end section and the second end section having greater strut length and greater strut width than the struts of the cylindrical element in the center section.

* * * * *

UNITED STATES PATENT AND TRADEMARK OFFICE
CERTIFICATE OF CORRECTION

PATENT NO. : 6,852,124 B2
DATED : February 8, 2005
INVENTOR(S) : Daniel L. Cox et al.

It is certified that error appears in the above-identified patent and that said Letters Patent is hereby corrected as shown below:

Column 8,
Line 38, delete "to,peak" and insert -- to peak --.

Column 11,
Line 24, delete "vessel-wall" and insert -- vessel wall --.

Column 14,
Line 15, delete "there," and insert -- there --.

Signed and Sealed this

Twenty-eighth Day of June, 2005

JON W. DUDAS
*Director of the United States Patent and Trademark Office*